US012109560B2

(12) United States Patent
Senetar et al.

(10) Patent No.: US 12,109,560 B2
(45) Date of Patent: Oct. 8, 2024

(54) STRIPPING OF REGENERATED CATALYST DURING START-UP AND SHUTDOWN

(71) Applicant: UOP LLC, Des Plaines, IL (US)

(72) Inventors: John J. Senetar, Naperville, IL (US); Richard A. Johnson, II, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 18/067,799

(22) Filed: Dec. 19, 2022

(65) Prior Publication Data

US 2023/0211332 A1 Jul. 6, 2023

Related U.S. Application Data

(60) Provisional application No. 63/295,632, filed on Dec. 31, 2021.

(51) Int. Cl.
| | |
|---|---|
| *B01J 38/12* | (2006.01) |
| *B01J 23/08* | (2006.01) |
| *B01J 23/92* | (2006.01) |
| *C07C 5/48* | (2006.01) |

(52) U.S. Cl.
CPC ............... *B01J 38/12* (2013.01); *B01J 23/08* (2013.01); *B01J 23/92* (2013.01); *C07C 5/48* (2013.01); *C07C 2523/08* (2013.01)

(58) Field of Classification Search
CPC ... B01J 38/12; B01J 23/08; B01J 23/92; B01J 23/62; B01J 38/30; B01J 38/34; B01J 23/96; C07C 5/48; C07C 2523/08; C07C 5/3337; Y02P 20/584
See application file for complete search history.

(56) References Cited

U.S. PATENT DOCUMENTS

| | | |
|---|---|---|
| 7,423,191 B2 | 9/2008 | Senetar et al. |
| 2002/0198428 A1* | 12/2002 | Iezzi ................. B01J 23/96 585/654 |
| 2011/0046424 A1 | 2/2011 | Pretz et al. |

FOREIGN PATENT DOCUMENTS

| | | |
|---|---|---|
| WO | 2013009820 A1 | 1/2013 |
| WO | 2017151361 A1 | 9/2017 |
| WO | 2017196586 A1 | 11/2017 |
| WO | 2020060700 A1 | 3/2020 |

OTHER PUBLICATIONS

PCT International Search Report PCT/US2022/082463, date of mailing Apr. 28, 2023.

* cited by examiner

*Primary Examiner* — Thuan D Dang
(74) *Attorney, Agent, or Firm* — Paschall & Associates, LLC; Mark Goldberg

(57) ABSTRACT

A process for preventing hazardous conditions at startup and shutdown of a reactor by sending an inert gas such as nitrogen to strip entrained oxygen from the catalyst when reactor temperatures are below about 240° C. During normal operation the entrained oxygen reacts with hydrocarbons to produce oxides but at the lower temperatures that are present at startup or shutdown these reactions do not occur sufficiently leaving oxygen that can cause hazardous conditions as temperatures increase upon startup. When the temperature is in the safe operating zone above 240° C., the nitrogen gas is stripped by air or other oxygen containing gas.

4 Claims, 1 Drawing Sheet

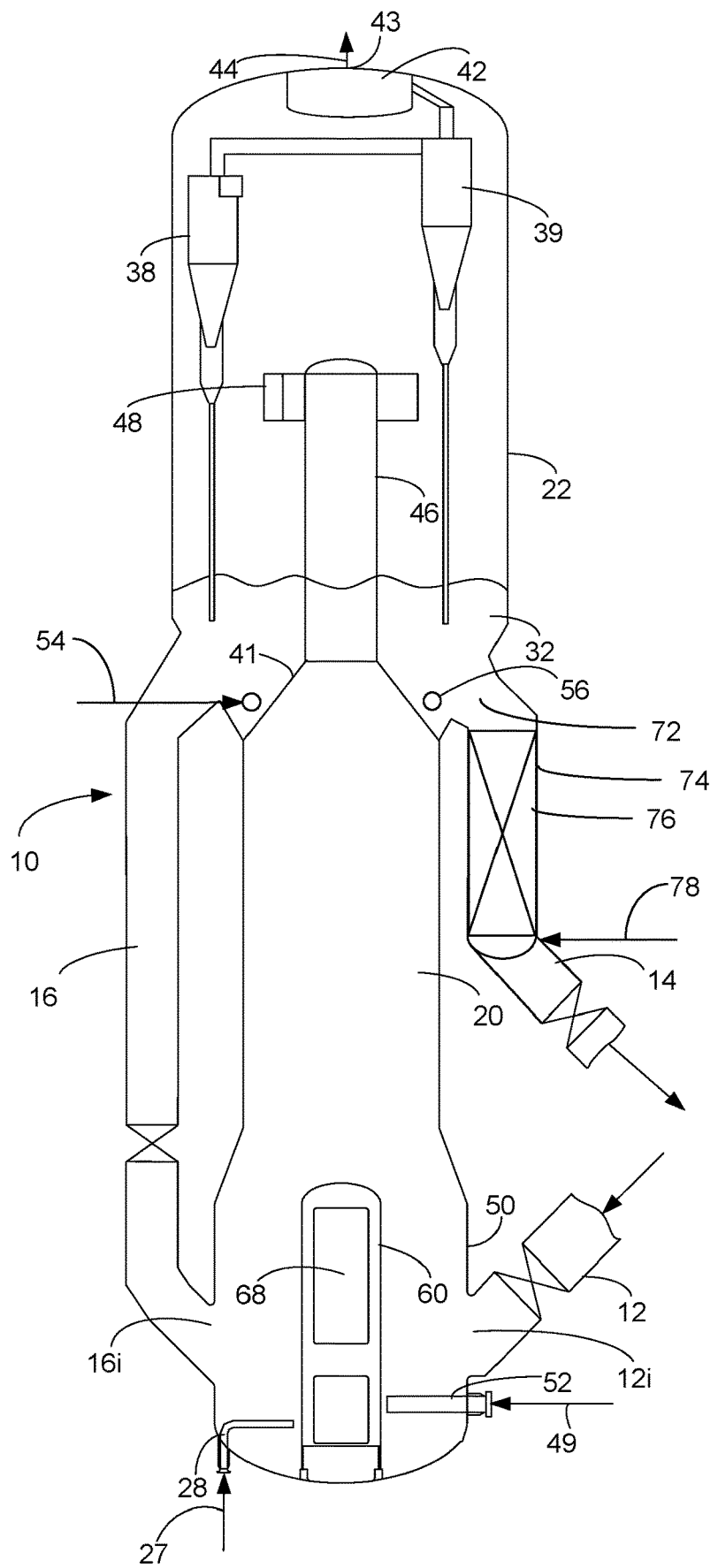

STRIPPING OF REGENERATED CATALYST DURING START-UP AND SHUTDOWN

CROSS-REFERENCE TO RELATED APPLICATIONS

This application claims priority from U.S. Provisional Application No. 63/295,632, filed Dec. 31, 2021, which is incorporated herein in its entirety.

FIELD

The field is the operation of a fluidized bed reactor and regeneration system at startup and shutdown.

BACKGROUND

Light olefin production is vital to the production of sufficient plastics to meet worldwide demand. Paraffin dehydrogenation (PDH) is a process in which light paraffins such as propane and butane can be dehydrogenated to make propylene and butylene, respectively. Dehydrogenation is an endothermic reaction which requires external heat to drive the reaction to completion.

In PDH reactions with fluidized catalyst, coke can deposit on the catalyst while catalyzing the reaction. The catalyst may be regenerated in a catalyst regenerator by combusting coke from the catalyst in the presence of oxygen. The hot regenerated catalyst may then be transferred back to the reactor to catalyze the reaction. However, the coke produced in the PDH reaction can provide insufficient heat from combustion in the regenerator to promote the endothermic dehydrogenation process. Hence, supplemental fuel such as fuel gas may be fed to the catalyst regenerator to heat the catalyst sufficiently to transfer sufficient enthalpy to drive the endothermic reaction. Conversely, if insufficient heat is provided to drive the endothermic reaction, olefin production can suffer.

Dehydrogenation catalyst may incorporate a dehydrogenation metal and a catalyst support such as alumina. The dehydrogenation metal comprises a noble metal present with gallium which is a highly active and selective catalyst metal function for dehydrogenation. The catalyst deactivates quickly within a cycle, so it is regenerated frequently. The frequent cycling between reaction and regeneration results in deactivation of the catalyst over time which must be restored. One way to regenerate the catalyst is carried out by first subjecting the catalyst to a combustion step with a low concentration of oxygen and subsequently reactivating the catalyst with a treatment in air or oxygen containing gas for longer than two minutes. However, Catalyst circulated to the reactor will entrain contacting vapor in the regenerator to the reactor. Under normal reactor conditions at high temperature (>240° C.), entrained oxygen containing gas will react with hydrocarbons to produce carbon monoxide and hydrogen and/or react with hydrogen to form water. During start-up and shutdown conditions when reactor temperatures are low, the oxygen in the entrained gas may not completely react with hydrocarbons and as a result create a potentially flammable mixture in the reactor and in downstream equipment. In addition, the circulation of light gases from the product back to the reactor can lead to accumulation of oxygen to the explosion limit. There is a need, therefore, for a solution that prevents oxygen from entering the reactor during start-up and shutdown to avoid a hazardous situation.

BRIEF SUMMARY

There is now provided a means to safely start-up and shutdown a paraffin dehydrogenation reactor without a concern of building up a flammable gas mixture in the reactor. Nitrogen stripping of the regenerated catalyst is employed when the reactor temperature is below a critical temperature of 240° C., but where oxygen will not react with the feed. Nitrogen stripping utilizes the same equipment installed for air stripping of the catalyst for reactivation. A control system can be employed to lock out the use of air in the stripper and replace the stripping medium with an inert gas such as nitrogen when conditions in the reactor are not adequate to insure complete combustion of entrained oxygen.

BRIEF DESCRIPTION OF THE DRAWINGS

The FIGURE is a schematic elevational drawing of a process of the present disclosure.

DEFINITIONS

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "fuel gas" comprises hydrocarbons, hydrogen and mixtures thereof.

The term "oxygen supply gas" comprises a gas comprising oxygen, such as air.

As used herein, the term "predominant" or "predominate" means greater than 50%, suitably greater than 75% and preferably greater than 90%.

DETAILED DESCRIPTION

The disclosure provides a process for avoiding oxygen from entering the reactor during start-up and shutdown to avoid a hazardous situation. As the temperature in the reactor is below about 240° C., oxygen that is entrained in the catalyst no longer will react with hydrocarbons that are present in the reactor. During start-up and shutdown conditions when reactor temperatures are low, the oxygen in the entrained gas may not completely react with hydrocarbons and therefore create a potentially flammable mixture in the reactor and downstream equipment. In addition, the circulation of light gases from the product back to the reactor can lead to accumulation of oxygen to the explosion limit. Nitrogen stripping of the regenerated catalyst is employed when the reactor is below 240° C. but preferably starting while the reactor is below 400° C. Nitrogen stripping utilizes the equipment installed for air stripping the catalyst during regeneration. A control system may be employed to lock out the use of air in the stripper and replace the air with nitrogen when conditions in the reactor are not adequate to insure complete combustion of the entrained oxygen.

The catalyst is regenerated by contact with a fuel gas and oxygen supply gas that is enriched in oxygen which sufficiently heats the catalyst by combusting coke on the catalyst and combusting the fuel gas. The regeneration restores catalytic activity to what it had before in the cycle of exposure to the paraffinic reactants in a dehydrogenation reactor. Activity is restored even on catalysts that deactivated despite accumulating negligible amounts of coke. The regeneration occurs despite the presence of large amounts of steam and carbon dioxide which are generated as combustion products.

The teachings herein may be applicable to any process that requires a gallium catalyst to be reheated and/or regenerated for an endothermic reaction. Paraffin dehydrogenation is an example of such a process. Dehydrogenation catalyst is used in a dehydrogenation reaction process to catalyze the dehydrogenation of ethane and/or propane to ethylene and propylene.

The conditions in the dehydrogenation reaction may include a temperature of about 500 to about 800° C., a pressure of about 40 to about 310 kPa and a catalyst-to-oil ratio of about 5 to about 100. The dehydrogenation reaction may be conducted in a fluidized manner such that gas, which may be the reactant paraffins or a fluidizing inert gas, is distributed to the reactor in a way that lifts the dehydrogenation catalyst in the reactor vessel while catalyzing the dehydrogenation of propane and/or butane. During the catalytic dehydrogenation reaction, coke is deposited on the dehydrogenation catalyst to reduce the activity of the catalyst. Other transformations such as reduction of the active sites may also deactivate some catalysts. The dehydrogenation catalyst must then be regenerated.

The use of the nitrogen stripping step is useful either in processes that use a separate air treatment after coke has been combusted from the catalyst and the catalyst heated sufficiently to transport sufficient enthalpy for the heat of reaction in the reactor or when the air stripping step is not needed due to use of an increasing oxygen concentration sufficiently in an oxygen supply gas provided for combustion of fuel gas in the presence of the catalyst and combustion of coke on the catalyst. After the temperatures have risen sufficiently on startup such as above 240° C., a stripping gas such as air is sent to the catalyst to remove the nitrogen gas.

The dehydrogenation catalyst selected should minimize cracking reactions and favor dehydrogenation reactions. Suitable catalysts for use herein include an active metal which may be dispersed in a porous inorganic carrier material such as silica, alumina, silica alumina, zirconia, or clay. An exemplary embodiment of a catalyst includes alumina or silica-alumina containing gallium, a noble metal, and an alkali or alkaline earth metal.

The catalyst support comprises a carrier material, a binder and an optional filler material to provide physical strength and integrity. The carrier material may include alumina or silica-alumina. Silica sol or alumina sol may be used as the binder. The alumina or silica-alumina generally contains alumina of gamma, theta and/or delta phases. The catalyst support particles may have a nominal diameter of about 20 to about 200 micrometers with the average diameter of about 50 to about 150 micrometers. Preferably, the surface area of the catalyst support is 85-140 m²/g.

The dehydrogenation catalyst may support a dehydrogenation metal. The dehydrogenation metal may be a one or a combination of transition metals. A noble metal may be a preferred dehydrogenation metal such as platinum or palladium. Gallium is an effective supporting metal for paraffin dehydrogenation. Metals may be deposited on the catalyst support by impregnation or other suitable methods or included in the carrier material or binder during catalyst preparation.

The acid function of the catalyst should be minimized to prevent cracking and favor dehydrogenation. Alkali metals and alkaline earth metals may also be included in the catalyst to attenuate the acidity of the catalyst. Rare earth metals may be included in the catalyst to control the activity of the catalyst. Concentrations of 0.001% to 10 wt % metals may be incorporated into the catalyst. In the case of the noble metals, it is preferred to use about 10 parts per million (ppm) by weight to about 600 ppm by weight noble metal. More preferably it is preferred to use 10-100 ppm by weight noble metal. The preferred noble metal is platinum. Gallium should be present in the range of 0.3 wt % to about 3 wt %, preferably about 0.5 wt % to about 2 wt %. Alkali and alkaline earth metals are present in the range of about 0.05 wt % to about 1 wt %.

The spent catalyst is transported to the catalyst regenerator vessel 10 to regenerate the spent catalyst into regenerated catalyst and to combust the coke if present. The catalyst regenerator vessel 10 includes a combustion chamber 20, which may be a lower chamber, and a separation chamber 22, which may be an upper chamber. The combustion chamber may include a mixing chamber 50 which mixes streams of catalyst and distributes gases to the catalyst. In the separation chamber 22, the regenerated catalyst is separated from flue gas generated in the combustion chamber 20. An oxygen supply gas distributor 52 provides oxygen supply gas from an oxygen supply gas line 49 to the combustion chamber 20. A plurality of oxygen supply gas distributors 52 may be employed to provide oxygen supply gas from the oxygen supply gas line 49 to the combustion chamber 20. A fuel gas distributor 28 distributes fuel gas from a fuel gas line 27 to the combustion chamber 20. Both gas streams lift the catalyst in the combustion chamber 20 into the separation chamber 22. A plurality of fuel gas distributors 28 may be employed to provide fuel gas from the fuel gas line 27 to the combustion chamber 20.

In an exemplary embodiment, the regenerator vessel 10 includes a mixing chamber 50. The mixing chamber may be located at a lower end of the of the combustion chamber 20 and the regenerator vessel 10. The mixing chamber 50 may include a spent catalyst pipe inlet 12i from the spent catalyst standpipe 12 which serves as an outlet for the spent catalyst standpipe. A spent catalyst standpipe 12 transports spent catalyst from the dehydrogenation reactor (not shown) to the catalyst regenerator vessel 10 through a control valve. The mixing chamber 50 may also include a regenerated catalyst pipe inlet 16i from a regenerated catalyst standpipe 16 which serves as an outlet for the regenerated catalyst standpipe. Heated regenerated catalyst from the separation chamber 22 may be transported back to the catalyst regenerator vessel 10 through a recycle regenerated catalyst standpipe 16 through a control valve to further heat catalyst in the regenerator vessel 10 by contact with hot regenerated catalyst.

The spent catalyst pipe inlet 12i discharges a stream of spent catalyst from a spent catalyst standpipe 12 into the mixing chamber 50, and the regenerated catalyst pipe inlet 16i discharges the recycled portion of regenerated catalyst from the regenerated catalyst standpipe 16 into the mixing chamber 50. The mixing chamber 50 receives a stream of spent catalyst and a stream of regenerated catalyst and mixes them together to provide a mixture of catalyst. While mixing, the hotter regenerated catalyst heats the cooler spent catalyst which serves to provide a heated catalyst mixture.

A mixing baffle 60 may be positioned within the mixing chamber 50 in an embodiment, to facilitate mixing between the spent catalyst and the regenerated catalyst. The mixing baffle 60 may comprise a capped cylinder with openings 68 opposed to catalyst inlets 12i or 16i.

An oxygen supply gas distributor 52 emits oxygen supply gas into the mixing chamber 50. The oxygen supply gas distributed from the oxygen supply gas distributor 52 includes oxygen necessary for combustion. The oxygen supply gas may also fluidize the catalyst within the mixing chamber 50 and lift the catalyst from the mixing chamber upwardly into the combustion chamber 20.

Coke on the spent catalyst may be insufficient to generate enough enthalpy from combustion to drive the endothermic reaction in the dehydrogenation reactor. In some cases, the catalyst may deactivate by a mechanism other than coke deposition and require oxidation to regenerate activity, even though very little or no detectable coke is on the spent catalyst. Moreover, higher regeneration temperature results in greater restoration of catalyst activity. Hence, supplemental fuel gas is added to the mixing chamber 50 in the regenerator vessel 10 to provide additional combustion enthalpy to drive the endothermic reaction in the dehydrogenation reactor and sufficiently restore catalyst activity. The regenerator vessel 10 may include a fuel gas distributor 28 for distributing fuel gas from fuel gas supply line 27 to the mixing chamber 50 for combustion in the combustion chamber 20. The fuel gas is combusted with oxygen in the oxygen supply gas in the presence of the catalyst to provide a heated, regenerated catalyst. Moreover, coke on catalyst is also combusted from the catalyst with oxygen in the oxygen supply gas to provide a regenerated catalyst. Combustion of coke and fuel gas generates flue gas. In an embodiment, the fuel gas and the coke on the catalyst are combusted together in the same vicinity, beginning in the mixing chamber 50 and then in the combustion chamber 20.

The superficial gas velocity in the mixing chamber 50 may about 0.9 m/s (3 ft/s), to about 5.4 m/s (18 ft/s), and the catalyst density may be from about 112 kg/m$^3$ (7 lb/ft$^3$) to about 400 kg/m$^3$ (25 lb/ft$^3$), preferably from about 48 kg/m$^3$ (3 lb/ft$^3$) to about 288 kg/m$^3$ (18 lb/ft$^3$), constituting a dense catalyst phase in the mixing chamber 50.

In an exemplary embodiment, a gas that has a higher concentration of oxygen than air is used as the oxygen supply gas. The concentration of oxygen in the oxygen supply gas should be greater than 21 vol %, suitably, between about 21 and about 40 vol % and preferably between about 22 and about 30 vol %. Air with 21 vol % oxygen is more concentrated than typical air streams because water typically is present in air at about 3 to about 6 vol %. Air enriched with oxygen may be used as the oxygen supply gas. The oxygen supply gas also may contain water, carbon dioxide, nitrogen, argon, and other atmospheric gases. In some embodiments the oxygen supply gas may contain between 2 and 6 vol % water.

Exemplary regeneration conditions in the combustion chamber 20 include a temperature from about 690° C. to about 800° C., preferably 705° C. to about 750° C. and a pressure of about 6.9 kPa (gauge) (1 psig) to about 450 kPa (gauge) (70 psig) in the combustion chamber 20.

Coke is deposited on the catalyst in the paraffin dehydrogenation reaction. The catalyst can comprise from 250 to about 1250 ppm carbon by weight and typically about 400 to about 1000 ppm carbon by weight. The coke is burned off the spent catalyst by contact with oxygen in the oxygen supply gas at regeneration conditions.

The oxygen concentration in the flue gas stream exiting the combustion chamber 20 should be greater than 4 vol %, preferably at least 5 vol %. The oxygen concentration in the flue gas stream exiting the combustion chamber 20 may be no more than 15 vol % and suitably no more than 12 vol %. The flue gas also comprises water and carbon dioxide generated by combustion of fuel gas and which enters with the oxygen supply gas stream. This results in significant amounts of water in the flue gas stream exiting the combustion chamber 20. For example, water concentration in the flue gas stream exiting the combustion chamber 20 may be typically greater than about 15 vol % and typically no more than about 25 vol %. The carbon dioxide concentration in the flue gas stream exiting the combustion chamber 20 typically may be between about 5 vol % and about 10 vol %. The flue gas stream exiting the regenerator vessel 10 in line 44 may have about the same oxygen concentration as that exiting the combustion chamber 20.

The fuel gas fed to the regenerator vessel 10 in line 27 may comprise about 6 to about 13 vol % of all the gases fed to the combustion chamber 20. The balance is the oxygen supply gas fed to the regenerator vessel 10 in line 49. Of all the gases fed to the combustion chamber 20 of the regenerator vessel 10, including oxygen supply gas and fuel gas, oxygen should comprise about should be about 20 to about 28 vol % of the gas.

Uncombusted fuel gas, flue gas, oxygen supply gas with a lower concentration of oxygen and catalyst ascend from the mixing chamber 50 through the combustion chamber 20. Catalyst, fuel gas and oxygen supply gas ascend in the combustion chamber 20 while coke is combusted from the catalyst and the fuel gas is combusted to regenerate and heat the catalyst and generate flue gas. The flow regime may be a fast-fluidized flow regime in which catalyst may slip relative to the gas and the gas can take indirect upward trajectories. The superficial velocity of the gases ascending in the combustion chamber 20 is preferably about 1.5 m/s (5 ft/s) to about 6 m/s (20 ft/s) and preferably about 2.1 m/s (7 ft/s) to about 5.4 m/s (18 ft/s), to provide a fast-fluidized flow regime. The catalyst density in the dilute catalyst phase in the combustion chamber 20 will be from about 16 kg/m$^3$ (1 lb/ft$^3$) to about 192 kg/m$^3$ (12 lb/ft$^3$).

The blend of gases and catalyst ascend from the combustion chamber 20 through a frustoconical transition section 41 into a riser 46 which has a smaller diameter than a major diameter of the combustion chamber 20. A blend of gases and catalyst accelerate in the narrower riser 46 and are discharged from a riser termination device 48 into the separation chamber 22. The transition section 41, the riser 46 and the riser termination device 48 are considered part of the combustion chamber 20. The riser termination device 48 may utilize centripetal acceleration to separate regenerated catalyst from flue gas. The superficial gas velocity in the riser 46 will be about 6 m/s (20 ft/s) to about 15 m/s (50 ft/s) and constitute a dilute catalyst phase.

Regenerated catalyst separated from flue gas by the riser termination device 48 drops into a dense catalyst bed 32. The catalyst separation chamber 22 may include one or more regenerator cyclones 38 or other solid/gaseous separator devices to separate the regenerated catalyst still entrained in the flue gas. In an aspect, primary cyclones 38 may collect flue gas from the separation chamber 22 and transport the flue gas separated from catalyst to a secondary cyclone 39 to further separate regenerated catalyst from the flue gas before directing secondarily purified flue gas to the plenum 42. Flue gas is discharged from the regenerator vessel 10 through an outlet 43 in a discharge line 44. Regenerated catalyst separated from flue gas in the cyclones 38, 39 is dispensed by dip legs into the dense catalyst bed 32.

A stream of fluidizing gas from bed gas line 54 may be distributed into the separation chamber 22 by a bed distributor 56 to fluidize regenerated catalyst in the dense catalyst bed 32. The fluidizing gas may be an oxygen supply gas such as air, or oxygen enriched air like used in the combustion chamber 20 or it may be inert such as steam or nitrogen.

A return portion of the regenerated catalyst collected in the dense bed 32 of the catalyst separation chamber 22 may be transported in the return regenerated catalyst standpipe 14 back to the dehydrogenation reactor ready for catalyzing dehydrogenation reactions. The return portion of the regenerated catalyst may exit the separation chamber 22 through an outlet 72 to enter the return regenerated catalyst standpipe 14. A stripper section 74 equipped with packing or stripping internals 76 may be provided to facilitate stripping of the regenerated catalyst with stripping gas from line 78 to flue gas or other gas entrained or adsorbed on the regenerated catalyst before it is returned to the dehydrogenation reactor through the return regenerated catalyst standpipe 14 at a rate governed by a control valve thereon. The stripping gas may be an oxygen supply gas such as air, or oxygen enriched air like used in the combustion chamber 20 during regular operations or in the practice of the disclosure herein, nitrogen is the preferred stripping gas to be used during startup and shutdown operations when entrained oxygen may stay unreacted on the catalyst. When the temperatures are then above 240 C and are expected to stay above that temperature, the nitrogen gas may then be stripped from the catalyst by use of air or other suitable gas.

A recycle portion of the regenerated catalyst collected in the dense bed 32 of the catalyst separation chamber 22 may be recycled in a recycle regenerated catalyst standpipe 16 back to the combustion chamber 20 of the regenerator vessel 10 via the mixing chamber 50. The regenerated catalyst is hotter and has a lower coke concentration than the spent catalyst fed to the regenerator vessel in standpipe 12.

The rate of recycle of regenerated catalyst can be controlled by operation of the control valve on the recycle regenerated catalyst standpipe 16 independently of the rate of spent catalyst to the regenerator vessel 10 by operation of the control valve on the spent catalyst pipe 12 to adjust the density of the catalyst. The density of the catalyst is directly proportional to the residence time of catalyst in the regenerator vessel 10 and particularly the residence time of the catalyst in the mixing chamber 50. Consequently, by adjusting the density of the catalyst in the mixing chamber 50 through varying the recycle rate of regenerated catalyst through the control valve on the recycle regenerated catalyst standpipe 16, the residence time of catalyst in the regenerator vessel 10 can be adjusted to ensure sufficient combustion and enthalpy absorbed by the catalyst and transferred to the dehydrogenation reactor.

The recycle rate of the regenerated catalyst through the recycle regenerated catalyst standpipe 16 to the mixing chamber 50 may be about 0.5 to about 5 times that of the rate of spent catalyst through the spent catalyst standpipe 12 to the mixing chamber. Suitably the recycle rate may be about 0.7 to about 3 times the rate of spent catalyst through the spent catalyst standpipe 12 to the mixing chamber 50.

The oxygen supply gas may be in contact with the spent catalyst for an average residence time of under about 2 minutes and preferably no more than about 90 seconds before initial separation in the riser termination device 48. Residence time of spent catalyst before initial separation or in the combustion chamber 20 begins with the spent catalyst entering the regenerator vessel 10 from the spent catalyst standpipe 12 and ends upon discharge from the riser termination device 48. Average residence time is calculated by the ratio of the volume of the regenerator vessel in question to the catalyst circulation rate. The volume of the regenerator vessel 10 upstream of separation includes the combustion chamber 20 which includes the mixing chamber 50, the transition section 41 and the riser 46. Due to catalyst recycle in the recycle standpipe 16, the average residence time for the spent catalyst per pass is the average residence time multiplied by the recycle ratio of the flow rate of recycle catalyst to the flow rate of spent catalyst fed to the combustion chamber 20. For example, if the recycle ratio is 1:1, the average residence time for the spent catalyst per pass is the average residence time multiplied by one-half. The average residence time per pass before initial separation should be no more than 1 minute and preferably no more than 45 seconds.

The oxygen supply gas may be in contact with the regenerated catalyst for an average residence time of under 1.5 minutes and preferably no more than 70 seconds after entering the separation chamber 22 after exiting the combustion chamber 20 and before exiting the regenerator vessel 10 through the return regenerated catalyst standpipe 14. Residence time of regenerated catalyst after entering the separation chamber 22 and before exiting the regenerator vessel 10 through the return regenerated catalyst standpipe 14 begins with the regenerated catalyst entering the separation chamber 22 from the riser termination device 48 and ends upon discharge from the regenerated catalyst stripper section 74. The volume of the regenerator vessel 10 downstream of separation includes the separation chamber 22 and the stripper section 74. Due to catalyst recycle in the recycle standpipe 16, the average residence time for the regenerated catalyst per pass is the average residence time in the separation chamber 22 multiplied by the recycle ratio of the flow rate of recycle catalyst to the flow rate of spent catalyst fed to the combustion chamber 20. However, the adjustment is not made for the stripper section 74. For example, if the recycle ratio is 1:1, the average residence time for the regenerated catalyst per pass is the average residence time in the separation chamber 22 multiplied by one-half plus the average residence time in the stripper section 74. The average residence time per pass before initial separation should be no more than 1 minute and preferably no more than 50 seconds.

The invention claimed is:

1. A process for regenerating a catalyst comprising noble metal and gallium comprising:
   feeding a stream of coked catalyst from a reactor to a regenerator vessel;
   feeding a stream of oxygen supply gas to said regenerator vessel;
   feeding a stream of fuel gas to said regenerator vessel;
   combusting coke from said coked catalyst and combusting said fuel gas with said oxygen supply gas to provide a regenerated catalyst and flue gas;
   separating said regenerated catalyst from said flue gas and transporting a return portion of the regenerated catalyst back to the reactor;
   stripping entrained oxygen on said regenerated catalyst before the regenerated catalyst is returned to the reactor by contacting said regenerated catalyst with an inert stripping gas during periods of startup or shutdown when temperature in said reactor is below 240° C.; and
   purging said inert stripping gas from said regenerated catalyst when temperature in said reactor is above 240° C.; wherein at least about 97 wt. % of said entrained oxygen is stripped from said regenerated catalyst by contacting said regenerated catalyst with said inert stripping gas; and
   wherein said inert stripping gas is completely purged from said regenerated catalyst after temperature in said reactor is maintained above about 400° C.

2. The process of claim 1 wherein at least about 99 wt. % of said entrained oxygen is stripped from said regenerated catalyst by contacting said regenerated catalyst with said inert stripping gas.

3. The process of claim 1 wherein said inert stripping gas comprises nitrogen.

4. The process of claim 1, wherein said inert stripping gas is purged from said catalyst by a flow of air.

\* \* \* \* \*